US008352056B2

(12) United States Patent
Lee et al.

(10) Patent No.: US 8,352,056 B2
(45) Date of Patent: Jan. 8, 2013

(54) SURGICAL IMPLANT GUIDE AND METHOD OF MANUFACTURING THE SAME

(75) Inventors: Shih-Tsen Lee, Taipei (TW); Chieh-Tsai Wu, Taipei County (TW); Heng-Liang Liu, Pingtung (TW); Ming-Yuan Tsai, Xinzhuang (TW)

(73) Assignee: Chang-Gung University, Taoyuan County (TW)

( * ) Notice: Subject to any disclaimer, the term of this patent is extended or adjusted under 35 U.S.C. 154(b) by 369 days.

(21) Appl. No.: 12/658,338

(22) Filed: Feb. 8, 2010

(65) Prior Publication Data

US 2011/0093023 A1 Apr. 21, 2011

(30) Foreign Application Priority Data

Oct. 21, 2009 (TW) ................................ 98135666 A

(51) Int. Cl.
*A61B 17/56* (2006.01)
*B23P 17/04* (2006.01)
(52) U.S. Cl. ............ 700/97; 700/98; 606/86 R; 623/901
(58) Field of Classification Search ................ 606/86 R; 623/901; 700/97, 98
See application file for complete search history.

(56) References Cited

U.S. PATENT DOCUMENTS

| 2006/0281046 A1* | 12/2006 | Heo ................................ 433/75 |
| 2008/0161815 A1* | 7/2008 | Schoenefeld et al. .......... 606/87 |
| 2009/0043556 A1 | 2/2009 | Axelson et al. |
| 2009/0254367 A1* | 10/2009 | Belcher et al. .................... 705/2 |

FOREIGN PATENT DOCUMENTS

| CN | 101390773 A | 3/2009 |
| TW | 545210 U | 8/2003 |
| TW | 200800123 A | 1/2008 |

* cited by examiner

*Primary Examiner* — Michael D Masinick
(74) *Attorney, Agent, or Firm* — Hudak, Shunk & Farine Co. LPA

(57) ABSTRACT

The present invention illustrates a method of manufacturing a surgical implant guide to increase the precision, safety and reliability of the surgery. First the present invention plans an invasive position for implanting an implant, and then, plans an invasive path for the implant to invade from the invasive position of an affected tissue, and finally, produces an implant guide based on the invasive position, the invasive path, and the shapes of the implant and the affected tissue. The surgical implant guide includes a coupling portion matching the shape the affected tissue, and a guiding portion matching the shape of the implant, the invasive position, and the invasive path. When the coupling portion is disposed on the affected tissue, the guiding portion is aligned with the invasive position, so that the implant is implanted in the affected tissue under guidance of the invasive path.

8 Claims, 6 Drawing Sheets

SURGICAL IMPLANT GUIDE AND METHOD OF MANUFACTURING THE SAME

FIELD OF THE INVENTION

The present invention relates to a surgical implant guide and a method of manufacturing the same; and more particularly, to an surgical implant guide and a method of manufacturing the same to enable implantation in an affected tissue in increased precision.

BACKGROUND OF THE INVENTION

Before performing a conventional orthopedic surgery, the surgeon would first observe images of the patient's affected bones obtained through X-ray photography or computerized tomography (CT), and then determines the manner of performing the surgery according to the surgeon's personal knowledge in anatomy and expertise in clinical surgery. Since lack of a precision guide as an aid for the surgery, it is difficult for the surgeon to precisely follow the preoperative planning and to perform the surgery. Therefore, the following four problems are found in the conventional orthopedic surgeries:

(1) the preoperative diagnosis and surgical path planning is less precise. In the event tissues nearby the affected part or the invasive path are injured, the patient is subject to serious impairment and complication caused by such imprecise diagnosis and surgical path planning. Further, if the surgeon fails to precisely indicate a relative position of the affected part, invasive path, and the surrounding tissues, the surgeon is frequently compelled to abandon the surgery.

(2) Due to the imprecise surgical path planning, a larger incision is usually made on the affected part of the patient's body to allow possible errors in the incision or to allow possible errors in the planned position at where an implant is to be implanted. Besides, the surgical instrument is invaded into the affected part via the incision. However, such errors would bring injury or impairment to the patient and even cause uncompensated serious injury. In recent years, the concept of minimal invasive surgery has been gradually adopted to various kinds of clinical surgeries. When the surgical incision or wound becomes smaller and smaller, the allowable errors in the invasive position and the surgical path are also reduced to further limit the use of the conventional surgical instruments.

(3) Experienced orthopedic surgeons are required to plan the invasive position and invasive path before the operations. Therefore, it would be difficult to control the surgical quality, such as the precision, safety and reliability of the surgery, when the surgery is performed by a surgeon with less experience.

(4) There are insufficient patient defect-related teaching models to serve as a learning aid in surgical teaching. Conventionally, since the performance of surgical procedures mostly relies on doctors' personal experiences, the surgical teaching can only be implemented through clinical teaching without assistance from related models of patients' deficiencies.

In brief, the conventional orthopedic operations mostly rely on surgeons' clinical experiences and suffer from imprecise, unsafe, and unreliable problems thereof. Further, there is no useful tool for determining the relation between the affected part and nearby tissues, rendering the whole surgical process to high uncertainty. It is therefore long felt need to develop a technique that can increase the precision, safety, and reliability of surgical operations and to reduce the surgical failure rate without highly relying on surgeons' personal clinical experience, such that the pressure of the surgeons in the clinical surgery can be relieved.

SUMMARY OF THE INVENTION

An object of the present invention is to provide a surgical implant guide to solve the problem of high uncertainty existed in the conventional orthopedic surgical process, so as to enable minimal incision, reduce chances of infection, and increase precision, safety and reliability of the surgery.

To achieve the above and other objects, the implant guide according to the present invention includes a coupling portion and at least one guiding portion. The coupling portion can be attached to a surface of an affected tissue. The guiding portion is connected to an outer surface of the coupling portion and provided with an implanting hole. When the coupling portion is disposed on the surface of the tissue, an end of the implanting hole is corresponding to an invasive position and the other end of the implanting hole is corresponding to a surgical incision at the affected part. Thus, an implant may be implanted in the affected tissue from the surgical incision to the invasive position of the affected tissue.

Another object of the present invention is to provide a method of manufacturing the surgical implant guide, so as to increase the precision, safety, and reliability in orthopedic and other implant surgeries.

To achieve the above and other objects, the method of manufacturing the implant guide includes the following steps: planning an invasive position and implanting an implant to an affected part of a patient's body at the invasive position; planning an invasive path wherein the implant invades in the affected part via the invasive path; and producing an implant guide based on the invasive position, the invasive path, the shape of the implant, and the shape of the affected part. The implant guide includes a coupling portion configured to match the shape of the affected part, and a guiding portion configured to match the shape of implant, the invasive position and the invasive path. When the coupling portion is disposed on the affected part, the implant guide is fitly attached on the affected part, and the guiding portion is aligned with the invasive position, so that the implant is implanted in the tissue at the affected part under guidance of the invasive path.

The implant guide and the method of manufacturing the same according to the present invention provide one or more of the following advantages:

(1) By using the implant guide as an aid in a surgical operation, tissues located nearby the affected part and having important functions, such as nerves and arteries and veins, can be protected against injury during the surgery. Therefore, the implant surgeries can be performed with increased precision, safety and reliability.

(2) The implant guide can be used as an aid in surgical teaching, and would be helpful in shortening the time required to learn and practice the implant surgeries, enabling interns and medical students to easily understand the implant surgeries.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
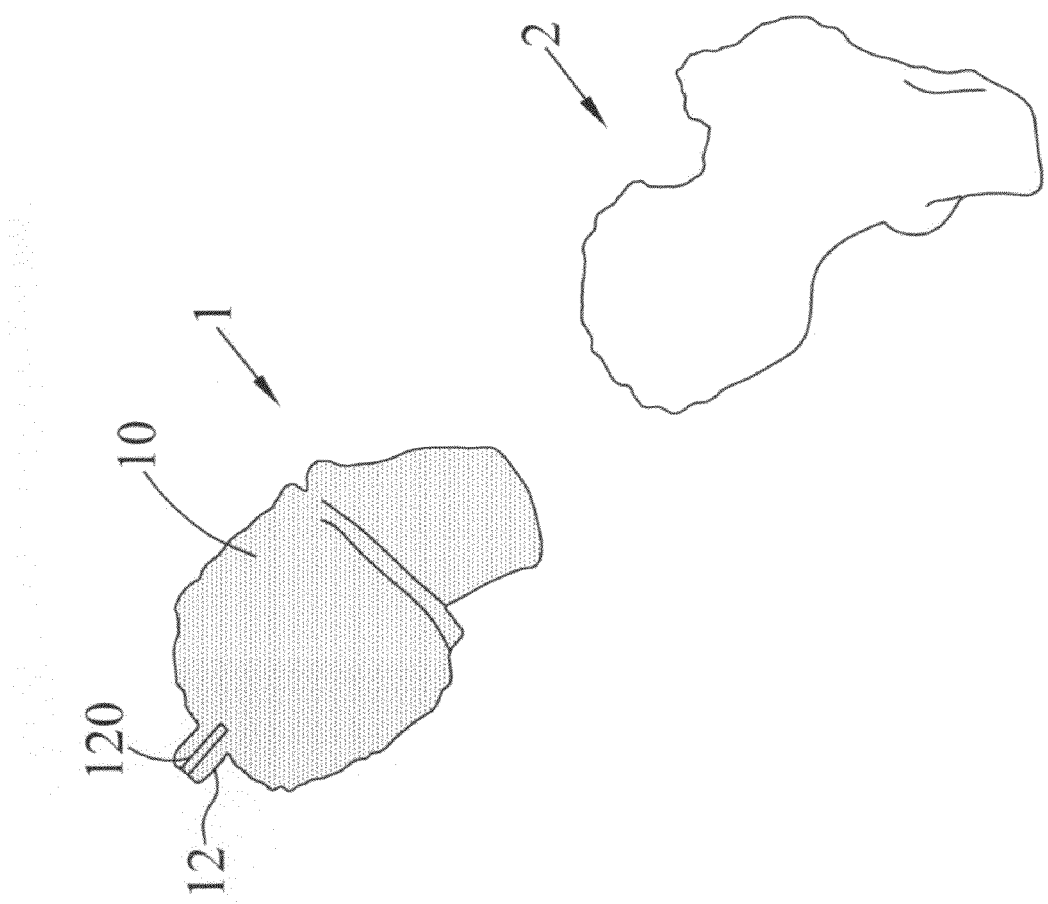
FIG. 1 is a schematic diagram of a surgical implant guide disposed on an affected left hip joint according to the present invention.

Please refer to FIG. 1 that is a schematic diagram of a surgical implant guide 1 according to the present invention for disposing on an affected part of a patient's body. For the purpose of conciseness, the present invention is also briefly referred to as "the implant guide" herein. As shown, the implant guide 1 includes a coupling portion 10 and at least one guiding portion 12. The coupling portion 10 is configured to match a surface structure of tissue 2 at the affected part and match an invasive position. The tissue 2 is invaded by an implant (not shown) from the invasive position. The guiding portion 12 is connected to an outer surface of the coupling portion 10 and includes an implanting hole 120 lengthwise extending through the guiding portion 12 into the coupling portion 10. The implanting hole 120 has an internal configuration matching an invasive path and the shape of implant wherein the implant invades into the tissue 2 via the invasive path. When the coupling portion 10 is disposed on the tissue 2, the coupling portion 10 would be fitly attached to the surface of the tissue 2; an end of the implanting hole 120 facing toward the tissue 2 would correspond to the invasive position on the tissue 2 for implanting the implant into the tissue 2, and another end of the implanting hole 120 facing away from the tissue 2 would correspond to a surgical incision made at the affected part of the patient's body.

Figure 2:
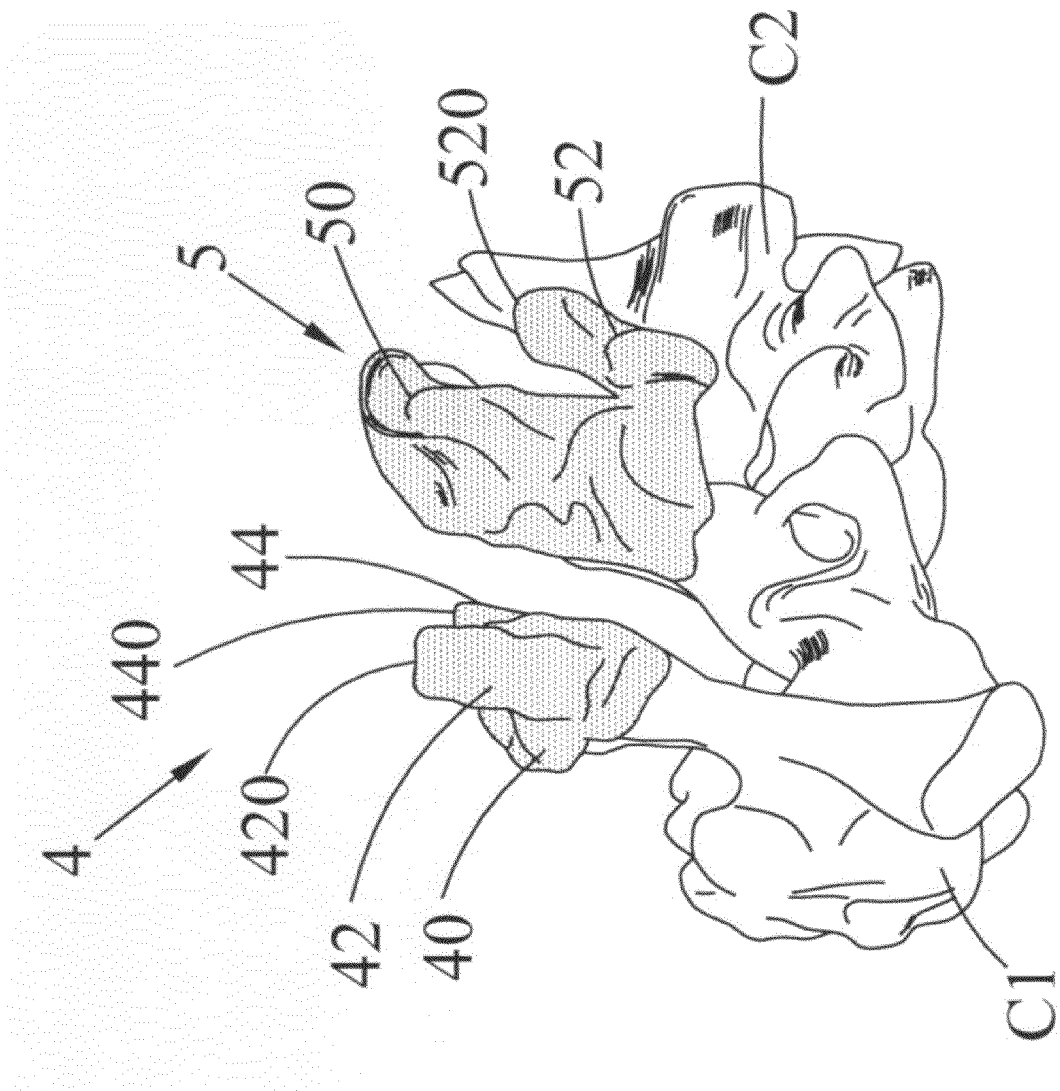
FIG. 2 is a schematic view showing the surgical implant guide disposed on affected cervical vertebras according to a first embodiment of the present invention.

Please refer to FIG. 2 that shows implant guide disposed on affected cervical vertebras according to a first embodiment of the present invention. That is, the implant guide according to the first embodiment of the present invention is applied to a surgery for implanting bone screws in cervical vertebral arches. In the illustrated first embodiment, the tissue undergoing surgery includes left and right vertebral arches of first cervical vertebra C1 and second cervical vertebra C2; and an implant, a bone screw in the illustrated first embodiment, is implanted in each of the left vertebral arches C1 and right vertebral arches C2. To perform the surgery, a first implant guide 4 and a second implant guide 5 according to the first embodiment of the present invention are separately disposed on the first cervical vertebra C1 and the second cervical vertebra C2. The first implant guide 4 has a first coupling portion 40 being configured to match the surface structural shape of the disposing position on the first cervical vertebra C1 and match the first invasive positions. A first and a second bone screw invade into the first cervical vertebra C1 at the first invasive positions. The second implant guide 5 has a second coupling portion 50 being configured to match the surface structural shape of the disposing position on the second cervical vertebra C2 and match the second invasive positions. A third and a fourth bone screw invade into the second cervical vertebra C2 at the second invasive positions.

The first implant guide 4 includes a first guiding portion 42 and a second guiding portion 44, and the second implant guide 5 includes a third guiding portion 52 and a fourth guiding portion (not shown in FIG. 2). The first guiding portion 42 is provided with a first implanting hole 420, which is internally configured to match the invasive path. Besides, the first bone screw invades into the first cervical vertebra C1 via the first invasive path. The second guiding portion 44 is provided with a second implanting hole 440, which is internally configured to match the invasive path. Besides, the second bone screw invades into the first cervical vertebra C1 via the second invasive path. The third guiding portion 52 is provided with a third implanting hole 520, which is internally configured to match the third invasive path; and the third bone screw invades into the second cervical vertebra C2 via the third invasive path. The fourth guiding portion is provided with a fourth implanting hole (not shown in FIG. 2), which is internally configured to match the fourth invasive path; and the fourth bone screw invades into the second cervical vertebra C2 via the fourth invasive path. The aforementioned term "invasive path" means angles and depths of a hole drilled on the cervical vertebra using a surgical instrument.

With the above arrangements, the first implant guide 4 and the second implant guide 5 can respectively disposed on the left and right vertebral arches of the first and the second cervical vertebra C1, C2; and the first and the second implanting hole 420, 440 formed on the first and the second guiding portion 42, 44 can separately correspond to the invasive positions on the left and right vertebral arches of the first cervical vertebra C1, and the third and the fourth implanting hole 520 formed on the third and the fourth guiding portion 52 can respectively correspond to the invasive positions on the left and right vertebral arches of the second cervical vertebra C2. Under guidance of the first, the second, the third and the fourth implanting hole 420, 440, 520, the surgical instrument, such as a surgical power drill, can drill into the left and right vertebral arches of the first and the second cervical vertebra C1, C2 at positions and angles and to depths defined by the predetermined invasive paths. Then, the first and the second implant guide 4, 5 are removed from the cervical vertebras C1, C2, and the first to the fourth bone screws can be implanted at correct angle, to correct depth and in correct position defined by respective invasive paths without injuring other important tissues, such as the nerve plexuses near the cervical vertebras. Thus, the cervical vertebral arch bone screw implantation surgery can be performed with increased precision, safety and reliability.

Figure 3:
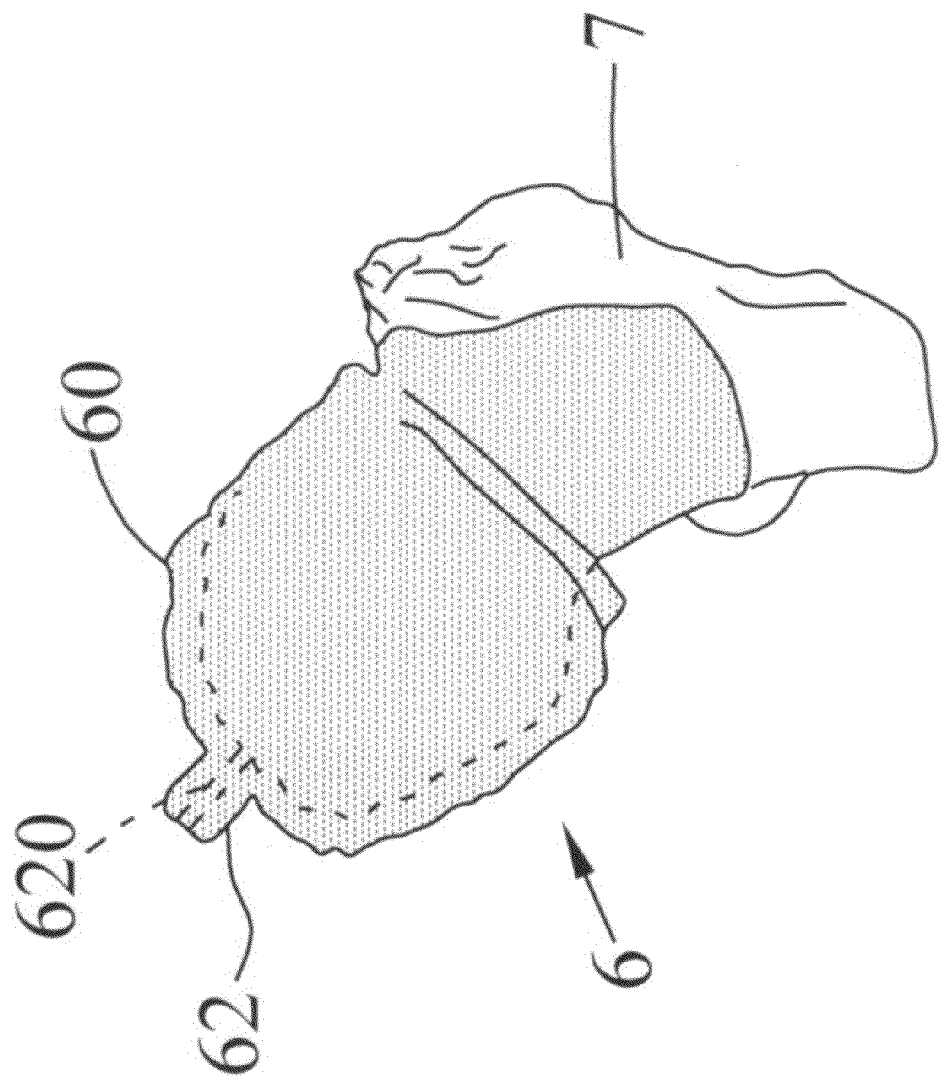
FIG. 3 is a schematic view showing the surgical implant guide disposed on an affected left hip joint according to a second embodiment of the present invention.

Please refer to FIG. 3 that shows an implant guide disposed on an affected left hip joint according to a second embodiment of the present invention. That is, the implant guide according to the second embodiment of the present invention is applied to the hip resurfacing arthroplasty. In the illustrated second embodiment, the tissue undergoing surgery is a femoral head 7 of a patient's left hip joint. To perform the hip resurfacing arthroplasty, first drill on the femoral head 7 along an axis of the femoral neck to provide a central line. Then, a surgical grinder is used along the central line to grind off necrotic tissue at the femoral head 7. Finally, a semispherical implant having a central post is implanted along the central line. In the illustrated second embodiment, the implant is an artificial joint, such as a metal ball for replacing the femoral head 7. Therefore, according to a second embodiment of the present invention, a third implant guide 6 is disposed on the left hip joint in the hip resurfacing arthroplasty. The third implant guide 6 has a third coupling portion 60 being configured to match a surface structural shape of the disposing position on the left hip joint and the invasive position, and the artificial joint is to be installed on the left hip joint at the invasive position. The third implant guide 6 also has a third guiding portion 62 provided with a fifth implanting hole 620. The fifth implanting hole 620 has an internal shape matching an invasive path; and the artificial joint is installed on the left hip joint via the invasive path. Under guidance of the fifth implanting hole 620, a surgical instrument, such as a surgical power drill, can drill into the femoral head to a position, at an angle and to a depth defined by the predetermined invasive path. Further, the surgical grinder is used together with the third implant guide 6 to remove necrotic tissue from the femoral head 7 to avoid injuring other important tissues, such as the remaining normal femoral head tissue. Thereafter, the artificial joint is fixed to the left femoral head. Thus, the left hip resurfacing arthroplasty can be performed with increased precision, safety and reliability.

While the implant guide of the present invention described in the first and the second embodiment are applied to the cervical vertebral arch bone screw implant surgery and the left hip resurfacing arthroplasty, it is understood the present invention is not limited to these usages but can also be applied to many other orthopedic surgical operations, including but not limited to spine fixation, total knee replacement (TKR), uni-knee replacement (UKR), total hip replacement (THR), half hip replacement, and bone fracture reconstruction, as well as dental implant and many other types of plastic surgery. Thus, the term "tissue" used herein can refer to any one of the cervical vertebral arches, the spines, the femoral heads of hip joints, and bones of knee joints.

Figure 4:
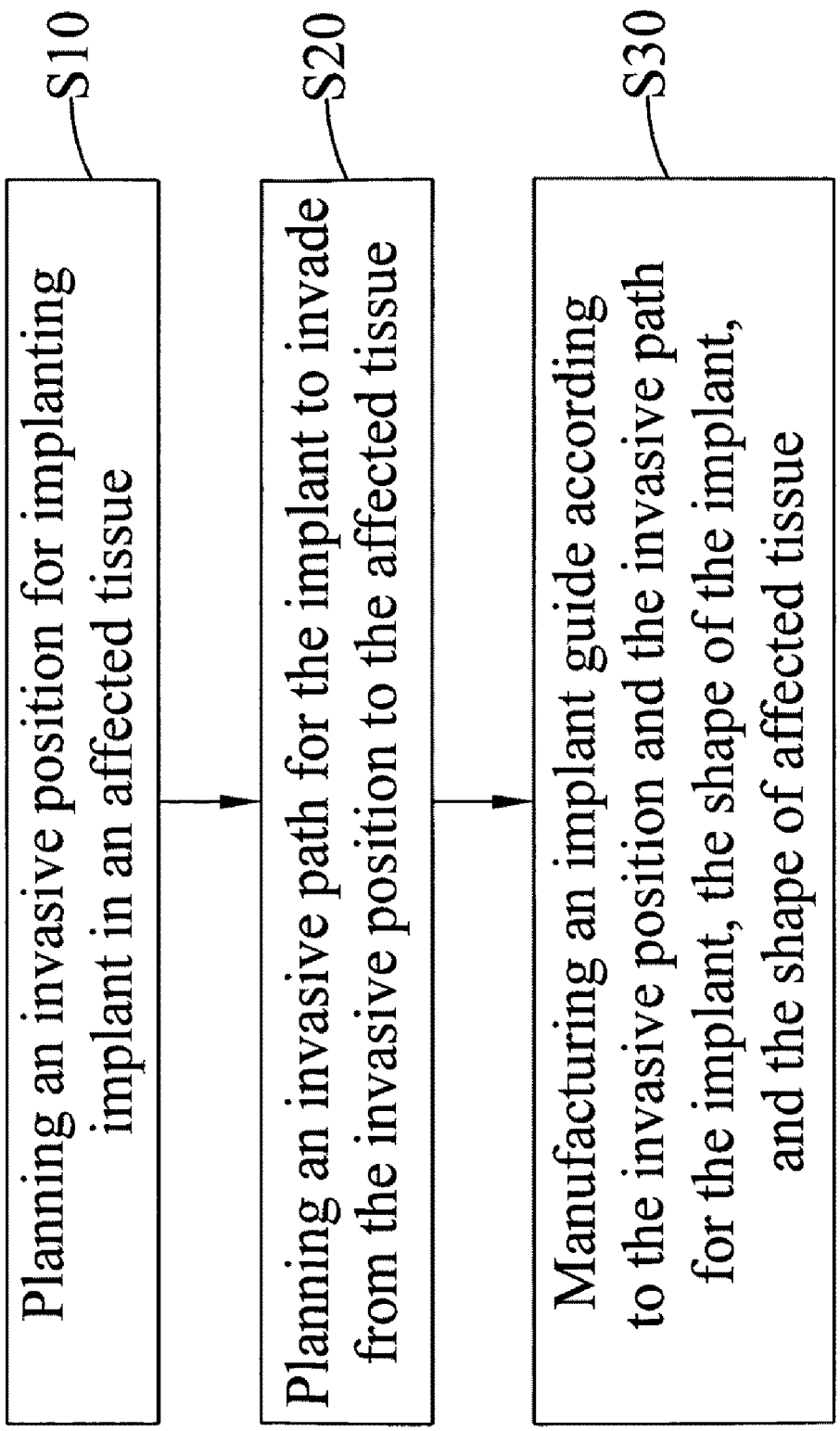
FIG. 4 is a flowchart showing the steps of manufacturing a surgical implant guide according to the present invention.

Please refer to FIG. 4 that is a flowchart showing the steps of manufacturing a surgical implant guide according to the present invention. As shown, to manufacture the implant guide of the present invention, following steps are included: (1) step S10: planning an invasive position wherein an implant is to be implanted in an affected tissue from the invasive position; (2) step S20: planning an invasive path wherein the implant invades from the invasive position into the affected tissue via the invasive path and (3) step S30: manufacturing an implant guide according to the invasive position, the invasive path for the implant, and a shape of the affected tissue. In the implant guide manufacturing method of the present invention, it is not necessary to perform the step S10 first. Instead, the step S20 can be performed before the step S10 is performed. The implant guide manufactured according to the above method includes a coupling portion matching the configuration of the tissue at the affected tissue and a guiding portion matching the invasive position and the invasive path for the implant. When the coupling portion of the implant guide is disposed on the affected tissue, the implant guide would fitly disposed on the affected tissue and the guiding portion would align with the invasive position, so that the surgical instrument is guided by the invasive path to complete the surgical procedures before implanting the surgical implant, enabling the implant to be precisely implanted in the affected tissue.

Figure 5:
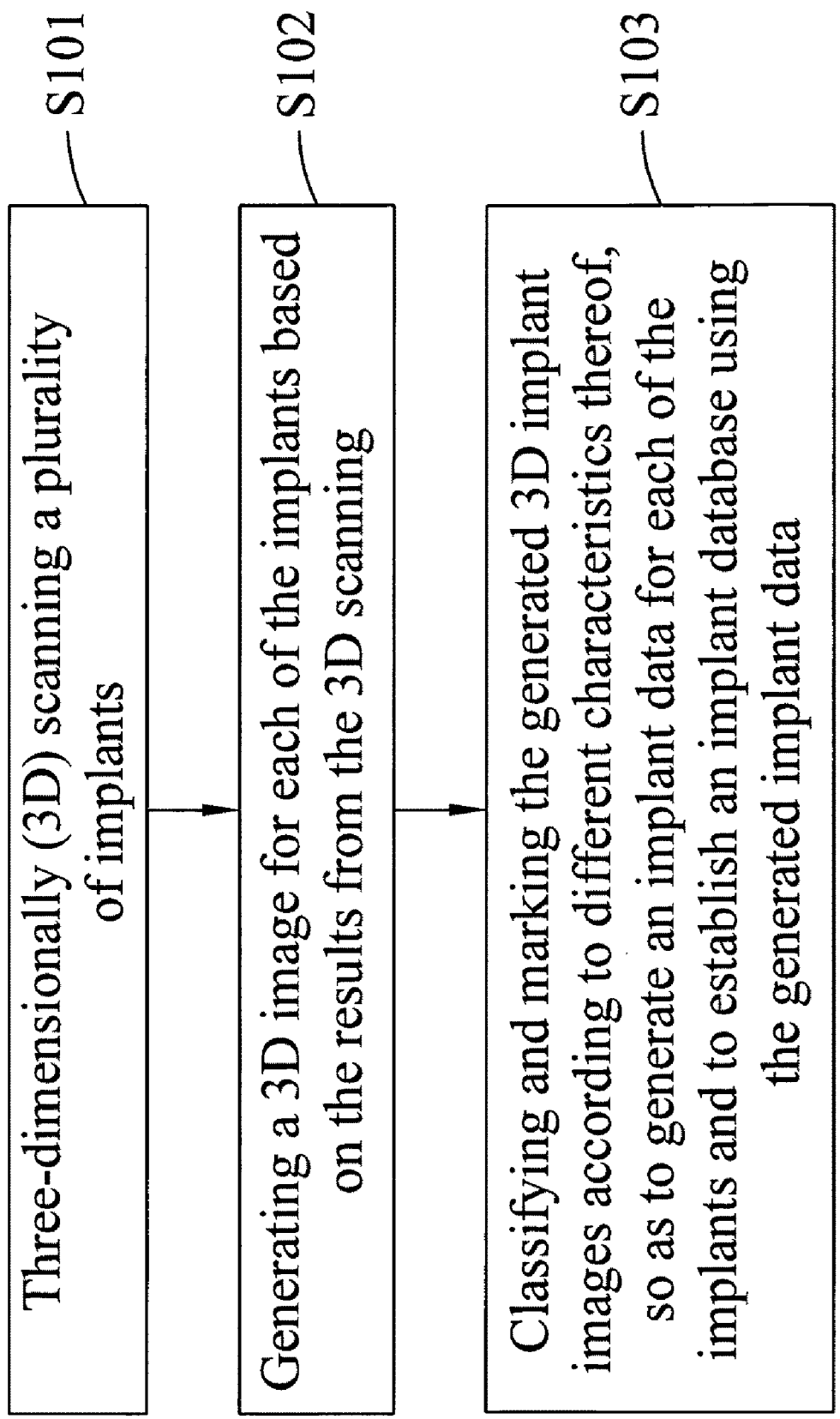
FIG. 5 is a flowchart showing the steps of the present invention for establishing an implant database.

According to the present invention, the method of manufacturing a surgical implant guide further includes steps of establishing an implant database before the step S10 of planning the invasive position or the step S20 of planning the invasive path. Please refer to FIG. 5 that is a flowchart showing the steps included in the method of the present invention for establishing the implant database: (1) step S101: three-dimensionally (3D) scanning a plurality of implants; (2) step S102: generating a 3D image for each of the implants based on results from the 3D scanning; and (3) step S103: classifying and marking the generated 3D implant images according to different characteristics thereof, such as the type, size and shape of the implants, so as to generate an implant data for each of the implants and to establish an implant database using the generated implant data.

Figure 6:
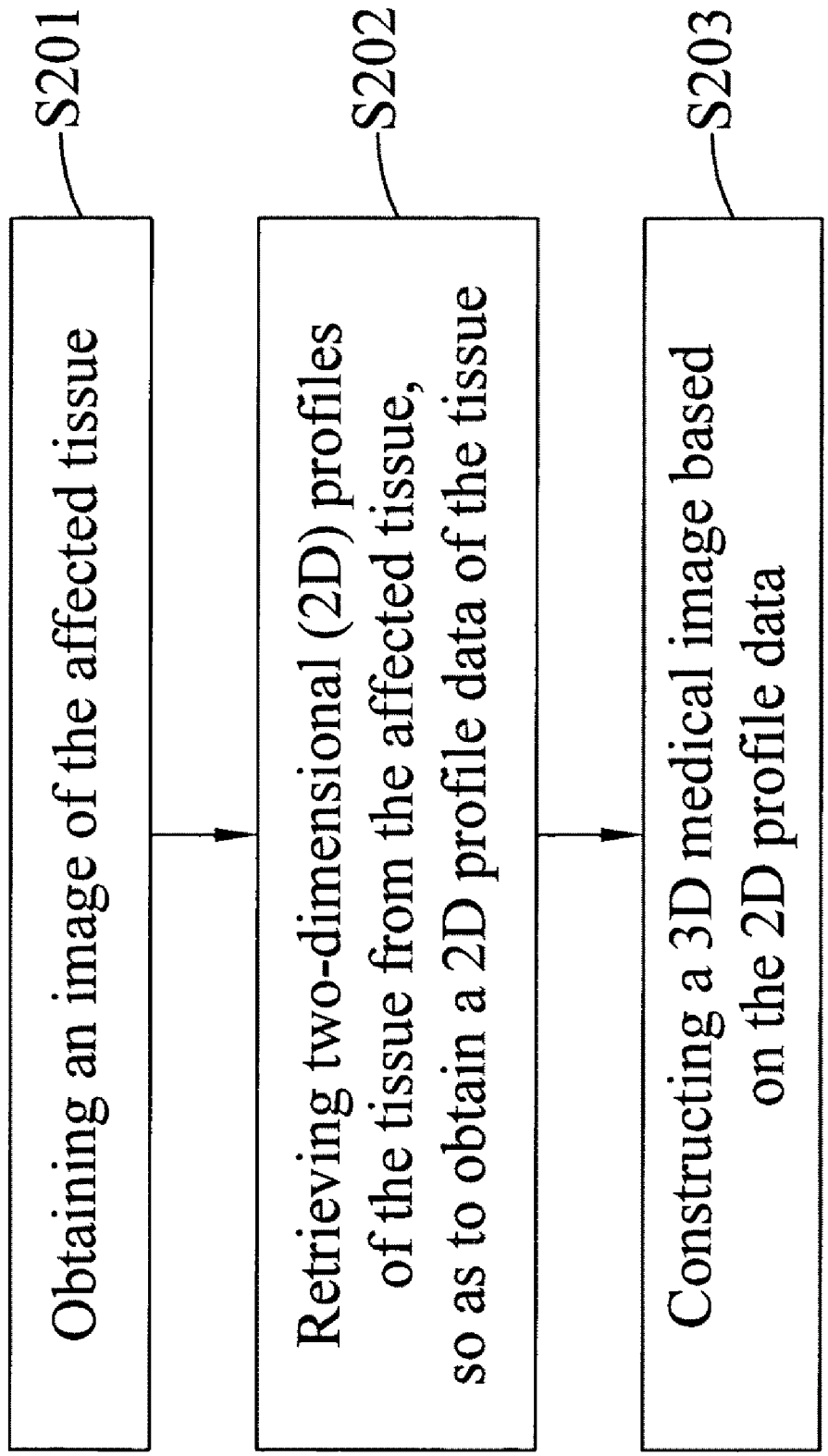
FIG. 6 is a flowchart showing the steps of the present invention for establishing an affected tissue image data.

According to the method of the present invention, the method of manufacturing a surgical implant guide further includes steps of establishing an affected tissue image data before the step S10 of planning the invasive position or the step S20 of planning the invasive path. Please refer to FIG. 6 that is a flowchart showing the steps included in the method of the present invention for establishing the affected tissue image data: (1) step S201: obtaining an image of the affected tissue through computerized tomography (CT) or X-ray photography; (2) step S202: retrieving two-dimensional (2D) profiles of the tissue from the affected tissue image, so as to obtain a 2D profile data of the tissue; and (3) step S203: constructing a 3D medical image based on the 2D profile data, and use the constructed 3D medical image as the affected tissue image data.

In the present invention, the 3D medical image of the tissue constructed based on the 2D profile data and the 3D implant images in the implant database is used as basis for planning the invasive position and the invasive path, as well as for producing 3D images of the implant guide. Thereafter, based on the 3D images of the implant guide, a customized implant guide may be manufactured using a 3D milling machine, a rapid prototyping machine, such as a 3D printer, and a 3D molding process.

According to the above description, it is understood that, in the present invention, in planning the invasive position for implanting an implant in an affected tissue or planning the invasive path, an implant database and data of an affected tissue image are used as basis, so that an implant most suitable for the affected tissue can be manufactured, such as the size and shape of the implant most suitable for the affected tissue. Thus, the planned invasive position and invasive path would not cause injury to the tissues nearby the affected part. Further, based on the implant shape, the invasive position and the invasive path obtained in the method of the present invention, it is able to manufacture an implant guide that can be disposed on the affected tissue properly.

In brief, in the present invention, an implant is determined according to the size and shape of an affected tissue, and a customized implant guide is developed according to the structure and relative position of the affected tissue, so that the implant guide is helpful in performing, for example, dental and orthopedic implant surgeries with increased precision, safety and reliability. Furthermore, the implant guide and the affected tissue structure model manufactured according to the present invention can be used in surgical training to enhance the efficiency in learning related surgical operations, shorten the required training time, and evaluate the results of surgical practices prior to a real surgical operation.

The present invention has been described with some preferred embodiments thereof and it is understood that many changes and modifications in the described embodiments can be carried out without departing from the scope and the spirit of the invention that is intended to be limited only by the appended claims.

What is claimed is:
1. A method of manufacturing a surgical implant guide, comprising the steps of:
establishing an implant database;
planning an invasive position for implanting an implant into the invasive position of an affected tissue;

planning an invasive path for the implant to invade from the invasive position of the affected tissue; and manufacturing an implant guide according to the invasive position and the invasive path for the implant, a shape of the implant, and a shape of the affected tissue;

wherein the shape of the implant is determined according to data from the implant database.

2. The method of manufacturing a surgical implant guide as claimed in claim 1, wherein the steps of establishing the implant database further comprises the steps of:

three-dimensionally scanning a plurality of implants;

generating a three-dimensional (3D) implant image for each of the plurality of implants based on results from the 3D scanning; and classifying and marking the generated 3D implant images according to different characteristics thereof, comprising the type, size, and shape of the implants.

3. The method of manufacturing a surgical implant guide as claimed in claim 2, further comprising a step of establishing an affected tissue image data before the step of planning the invasive position or the step of planning the invasive path.

4. The method of manufacturing a surgical implant guide as claimed in claim 3, wherein the step of establishing the affected tissue image data comprises:

obtaining an image of the affected tissue;

retrieving two-dimensional (2D) profiles of the affected tissue from the image of the affected tissue for obtaining a 2D profile data of the affected tissue; and constructing a 3D medical image based on the 2D profile data, and using the constructed 3D medical image as the affected tissue image data.

5. The method of manufacturing a surgical implant guide as claimed in claim 4, wherein the image of the affected tissue is obtained through any one of computerized tomography (CT) and X-ray photography.

6. The method of manufacturing a surgical implant guide as claimed in claim 5, wherein the step of planning the invasive position or the step of planning the invasive path further comprises the step of using the implant database and the affected tissue image data to obtain the implant according to different characteristics of the affected tissue; the characteristics of the affected tissue comprising size, shape and the like of the tissue, and to plan the invasive position and the invasive path for the implant.

7. The method of manufacturing a surgical implant guide as claimed in claim 6, further comprising a step of producing a 3D image of the surgical implant guide based on the 3D medical image and the 3D implant images.

8. The method of manufacturing a surgical implant guide as claimed in claim 7, further comprising a step of manufacturing the implant guide based on the 3D image of the implant guide using a 3D milling machine, a rapid prototyping machine, or a 3D molding process.

* * * * *

UNITED STATES PATENT AND TRADEMARK OFFICE
CERTIFICATE OF CORRECTION

PATENT NO. : 8,352,056 B2  Page 1 of 1
APPLICATION NO. : 12/658338
DATED : January 8, 2013
INVENTOR(S) : Shih-Tseng Lee et al.

It is certified that error appears in the above-identified patent and that said Letters Patent is hereby corrected as shown below:

Title Page;
In section (75) Inventors, the first named inventor should read "Shih-Tseng Lee". The patent currently presents the first name of the first inventor as "Shih-Tsen".

Signed and Sealed this
Ninth Day of April, 2013

Teresa Stanek Rea
*Acting Director of the United States Patent and Trademark Office*